(12) United States Patent
Steinmüller-Nethl et al.

(10) Patent No.: US 8,753,661 B2
(45) Date of Patent: Jun. 17, 2014

(54) BIOLOGICAL SURFACES

(75) Inventors: Doris Steinmüller-Nethl, Rinn/Aldrans (AT); Detlef Steinmüller, Rinn/Aldrans (AT); Frank Rudolf Kloss, Innsbruck (AT); Robert Gassner, Innsbruck (AT); Günther Bonn, Zirl (AT); Christian Wolfgang Huck, Innsbruck (AT); Muhammed Najam-Ul-Haq, Innsbruck (AT); Matthias Rainer, Grinzens (AT); Günther Stecher, Götzens (AT)

(73) Assignee: Diacoating GmbH, Innsbruck (AT)

( * ) Notice: Subject to any disclaimer, the term of this patent is extended or adjusted under 35 U.S.C. 154(b) by 1408 days.

(21) Appl. No.: 11/792,613

(22) PCT Filed: Dec. 7, 2005

(86) PCT No.: PCT/AT2005/000495
§ 371 (c)(1),
(2), (4) Date: Sep. 25, 2007

(87) PCT Pub. No.: WO2006/060836
PCT Pub. Date: Jun. 15, 2006

(65) Prior Publication Data
US 2008/0044451 A1 Feb. 21, 2008

(30) Foreign Application Priority Data

Dec. 7, 2004 (AT) ............... A 2063/2004

(51) Int. Cl.
| | |
|---|---|
| A61F 2/00 | (2006.01) |
| A61L 27/30 | (2006.01) |
| A61L 27/54 | (2006.01) |
| A61L 29/10 | (2006.01) |
| A61L 29/16 | (2006.01) |
| A61L 31/08 | (2006.01) |

(52) U.S. Cl.
CPC ............... *A61L 27/303* (2013.01); *A61L 27/54* (2013.01); *A61L 29/103* (2013.01); *A61L 29/16* (2013.01); *A61L 31/084* (2013.01)
USPC ....................................................... 424/423

(58) Field of Classification Search
None
See application file for complete search history.

(56) References Cited

U.S. PATENT DOCUMENTS

| | | | |
|---|---|---|---|
| 4,504,519 A | 3/1985 | Zelez | |
| 5,404,835 A * | 4/1995 | Yoder | ............... 117/79 |

(Continued)

FOREIGN PATENT DOCUMENTS

| | | |
|---|---|---|
| AT | 399 726 B | 7/1995 |
| AT | 500 618 A4 | 2/2006 |

(Continued)

OTHER PUBLICATIONS

Yafei et al, "Surface Free Energies and Morphologies of Chemical Vapor Deposited Diamond Films" Chin.Phys.Lett., vol. 11, No. 8, (1994), p. 502-505.*

(Continued)

*Primary Examiner* — Bethany Barham
(74) *Attorney, Agent, or Firm* — Laurence A. Greenberg; Werner H. Stemer; Ralph E. Locher

(57) ABSTRACT

A base body contains a substrate that is at least partially coated with a carbon-containing layer. The carbon-containing layer is at least partially functionalized with a molecule that is bound directly or via at least one linker or functional group to the carbon-containing layer. The base body, which has a functionalized carbon-containing surface, is capable of influencing biological processes during a corresponding functionalization.

27 Claims, 5 Drawing Sheets

(56) References Cited

U.S. PATENT DOCUMENTS

| | | | |
|---|---|---|---|
| 5,716,404 A | 2/1998 | Vacanti et al. | |
| 5,755,788 A | 5/1998 | Strauss | |
| 6,129,928 A | 10/2000 | Sarangapani et al. | |
| 6,383,215 B1 | 5/2002 | Sass | |
| 6,447,295 B1 | 9/2002 | Kuamar et al. | |
| 6,494,916 B1 * | 12/2002 | Babalola et al. | 623/23.3 |
| 6,565,913 B2 | 5/2003 | Arps et al. | |
| 2003/0031872 A1 | 2/2003 | Arps et al. | |
| 2003/0191533 A1 * | 10/2003 | Dixon et al. | 623/17.14 |
| 2003/0199741 A1 | 10/2003 | Martinez | |
| 2004/0198049 A1 | 10/2004 | Dahl et al. | |
| 2004/0261702 A1 | 12/2004 | Grabowy et al. | |
| 2005/0079201 A1 * | 4/2005 | Rathenow et al. | 424/424 |
| 2005/0165485 A1 * | 7/2005 | Trieu | 623/17.13 |
| 2006/0150862 A1 | 7/2006 | Zhao et al. | |
| 2006/0240062 A1 | 10/2006 | Hellerbrand et al. | |

FOREIGN PATENT DOCUMENTS

| | | |
|---|---|---|
| DE | 101 07 795 A1 | 8/2002 |
| DE | 101 52 055 A1 | 5/2003 |
| DE | 102 16 971 A1 | 10/2003 |
| EP | 0 302 717 A1 | 2/1989 |
| EP | 0 376 694 A2 | 7/1990 |
| JP | 1-157498 | 6/1989 |
| JP | 2-92895 | 4/1990 |
| WO | 98/02100 | 1/1998 |
| WO | WO 02/080996 A1 | 10/2002 |
| WO | WO 03/035924 A1 | 5/2003 |
| WO | WO 2004/006977 A2 | 1/2004 |
| WO | WO 2004/024199 A1 | 3/2004 |
| WO | WO 2004/024201 A2 | 3/2004 |
| WO | 2005/096346 A3 | 10/2005 |

OTHER PUBLICATIONS

Hauert, R.: "A review of modified DLC coatings for biological applications", Elsevier Publishers, Amsterdam, NL, pp. 583-589, 2003.

Lasseter, T.L. et al.: "Covalently Modified Silicon and Diamond Surfaces: Resistance to Nonspecific Protein Adsorption and Optimization for Biosensing", Journal of the American Chemical Society, U.S.A., pp. 10220-10221, Jul. 30, 2004.

* cited by examiner

BIOLOGICAL SURFACES

BACKGROUND OF THE INVENTION

Field of the Invention

The present invention relates to base bodies which are particulary suitable for the use as implants, surgical instruments and cell-growth vessels.

In biomedical science the field of tissue technology, the so-called tissue engineering or cell engineering, is a new attractive and promising method having different aims:

1. Cells shall be cultured and propagated to be optionally inserted into a patient;
2. Tissue shall be cultured in vitro to allow for studies and analysis;
3. Growth and organic function shall be influenced in vitro and in vivo by biomolecules, proteins.

In this context, the use of the most different proteins or biomolecules, which shall influence and modulate cell growth in vitro and in vivo, plays a special role. Said proteins can be of endogenous (form themselves in the body) or exogenous (created by external factors) origin.

The introduction said proteins or biomolecules into the cell culture or into the organism may occur in various ways. In the cell culture, such proteins are given into the culture medium, and are, thus, presented to the cells in the culture. This starts a not directly influenceably process. This procecedure corresponds in vivo to a systemic administration of a drug or a protein. In tissue engineering such a systemic administration is, as a rule, not desired, drug administration excepted, as mostly local, organ-specific effects shall be achieved. Therefore, different methods for transporting proteins to their site of action are described in the literature.

The most simple method is the local application of proteins, biomolecules or substrates at the desired site of action. This may be achieved, e.g. by suspending these substances in a liquid, which is subsequently dried on to a carrier which, finally, shall be introduced into the organism (AU 688406; WO 2004/024199). With this technique of application a systemic effect cannot be avoided because of the present local blood circulation and diffusion processes. A further disadvantage is that due to this "single shot", with local applications, the effect is limited to a short period of time and higher concentrations are necessary. Therefore, systems have been developed which allow for introduction of the proteins into the organism and, at the same time, for their delayed release. One method is the use of so-called "slow releasing systems" or "biomimetic coatings" (WO 2004/024201; U.S. Pat. No. 6,129,928; CN 1393218). There, proteins or similar active substances can be embedded into an absorbable and/or degradable material and be introduced into the organism. There, the proteins are then released gradually by dissolving the carrier substance. Thus, a delayed release of the substances used results, a single-shot effect can be avoided, a systemic effect, however, not.

The transfer of gene segments constitutes an alternative technique. Stationary cells shall thereby be stimulated to secret a certain protein or to differentiate themselves. The use of vectors, including mainly adenoviruses, has proven to be particularly efficient. The viruses are referred to as vectors, since they are the transferrers of the respective gene segment. A prerequisite for the use of the viruses for gene transfer is to prevent both the activation of viral promoters and the progression of the lytic infection, i.e. to prevent the target cells from being killed. Nevertheless, direct infection of the target tissue shall still remain possible, thus allowing for gene transfer. These conditions can be reached, e.g., in the adenovirus by deleting certain virus-specific gene segments. Despite deletion of gene segments detrimental to the organism, viral gene products are found in cells which have been infected with adenovectors. Vectors can also be introduced into cells by the use of liposomes, infectivity not being given (U.S. Pat. No. 5,755,788). Liposomes can be bound to surfaces, thus achieving an activation of the surrounding tissue (Thorwarth M et al., Mund Kiefer Gesichtschir. (2004); 8:250-255).

The decisive advantage of this therapy form is the fact that an expression of the transferred gene is possible over a longer period of time as compared to conventional carrier materials. After a very high initial expression, production of the transferred genes in most cases reduces only after about 4 weeks. This method has already been used in therapeutic approaches to the treatment of mucoviscidosis.

All of the methods described involve the disadvantageous effect that a systemic effect cannot be avoided by applying and/or releasing the substances introduced. Furthermore, doses above the physiological needs are required to compensate for the removal, e.g. away from a base body used as implant, surgical instrument or cell-growth vessel.

Such drug-release systems are used in implantology. DE 10216971, e.g., discloses a medical implant which discloses a bio-compatible surface consisting of a carbon-containing layer and a drug-release system. Also in this case, the concentration of the active substances released on the surface reduces over a short period of time to a level which cannot cause any or no sufficient effect in the body any longer.

WO 02/080996 A1 describes a coating of medical implants with a diamond-like carbon coating. Said coating is additionally provided with a bio-degradable coating, into which medically relevant substances have been introduced. These substances shall be released in a controlled manner.

DE 101 07 795 A1 describes, among others, a method for reducing sequelae after implanting stents. In order to reduce such complications, substances, preferably 17β-estradiol, are provided on the implant which prevent growth of non-striated musculature and, at the same time, promote development of the endothelium. During implant healing the active substance 17β-estradiol shall be released.

US 2004/0198049 relates to the use of materials comprising diamondoid in microelectronics.

WO 2003/035924 discloses a substrate provided with a coating comprising amorphous carbon, on which metallic ions are immobilised which show an antimicrobial effect.

US 2003/0199741 concerns a medical device provided with diamonds, DLC, borosilicate, carbides and nitrides. Therein, a catheder is also arranged for which comprises a diamond or DLC coating.

WO 1998/02100 relates to implants provided with a thrombo-resistent material, wherein coatings which comprise DLC are considered particularly advantageous. According to this document antithrombogenic or thrombogenic active substances can be applied either directly or via a further coating, such as, e.g., bio-degradable matrices.

DE 101 52 055 discloses a method for deposition of mechanically and thermodynamically stable amorphous carbon coatings by the aid of a low-pressure-plasma deposition method. Among others, the possibility of using amorphous carbon coatings, onto which a pharmaceutical active substance has been applied, is mentioned Carbon-containing layers are often used for coating implants, since such layers have a high biocompatibility and, thus, reduce rejection reactions to such a great extent that partly no such reactions are provoked any longer. Moreover, carbon-containing layers have also proven to be robust and to have low friction (U.S. Pat. No. 6,447,295; EP 0 302 717).

SUMMARY OF THE INVENTION

Therefore, it is an object of the present invention to provide bio-compatible base bodies, in particular cell-growth vessels and medical means, such as implants and surgical instruments, allowing for substances, such as, e.g., biomolecules, such as proteins, hormones, carbons, which cause a reaction in the human and animal body as well as also in the cell-growth vessel, to be exposed to the environment at a pre-defined site in a predetermined concentration over a long period of time, in order to promote, e.g., growth of cells, in particular body cells, or ossification after fractures. A further object of the present invention is to provide medical means which are highly acceptable in the body of a mammal, and, thus, provoke no or very little negative body reactions (e.g. rejection reactions), wherein, for example, an enhancement of osseointegration can also be induced.

Therefore, the present invention relates to a base body comprising a substrate which is at least partially coated with a carbon-containing layer, wherein the carbon-containing layer is at least partially functionalised with a molecule which is bound to the carbon-containing layer either directly or via at least one linker.

According to the invention "base body" refers to bodies which may be coated with a carbon-containing layer, wherein the layer itself may also be functionalised. Targets as used, e.g., in mass spectrometry, are not referred to as base bodies in the sense of the present invention and, thus, are not covered by this term (compare AT-A-589/2004).

The carbon atoms of the coating allow for a covalent binding of molecules, such as, e.g., proteins or other biomolecules, or of linkers, to which biomolecules may be bound covalently or non-covalently, to the carbon-containing layer and, thus, to the base body, in particular to the implant and/or surgical instrument (compare AT-A-589/2004). There, the carbon-containing layer must be applied on a base body such that the microtexture and porosity of the base body surface will not be disturbed. This is decisive for osseointegration, i.e. for the implant-healing of such base bodies in the bone when used as implants, since it could be shown in numerous studies that especially a microstructured surface allows for immigration of osteocytes into the surface (Buser D. et al., J Dent Res (2004) 83: 529-533) and only thereby an osseointegration is achieved. In AT 399726 B, e.g., a method is described with which it is feasible to apply nanocrystalline pure diamond layers on surfaces, in order to meet the requirements imposed on base bodies. As the carbon atoms function as binding site for molecules the surface of the base bodies at least partially consists of carbon after coating. Thus, many binding sites are provided, allowing for not only one molecule but a large number of different molecules to be bound to the surface. For example, the concentration of the desired molecules can be thus reduced by combination with placebo molecules (molecules without any biological effect; competetive binding of the placebo molecules and the biologically effective molecules) and can be adapted to the local physiological demands.

The "substrate" itself as a shaping component of the base body may consist of any materials suited as carriers for carbon-containing layers and for base bodies, wherein the substrates may be both electrically conductive or electrically nonconductive.

"Functionalised" in the sense of the present invention means that a functional molecule (e.g. a protein) is bound to the surface of a base body such that a diffusion away of the molecule introduced is substantially not possible or to a very little extent only, and, thus, a systemic effect may be avoided. For example, a diamond-layer surface is ideally suited for binding proteins (Nature Materials 3, 736-742 (1 Oct. 2004). The carbon atoms can be broken down by chemical or physical methods such that functional groups can be bound. A local effect is ensured by chemical binding. Biological activity of the molecules, in particular of the proteins, is not influenced by the covalent binding to the carbon-containing surface and, thus, can unfold locally (Nature Materials 3, 736-742 (1 Oct. 2004). Molecules can be bound to the carbon-containing surface not only by covalent but also by non-covalent bindings, provided that the binding is strong enough so that a diffusion away, under physiological conditions, is in a limited range or not possible (compare biotin-streptavidin binding).

According to the invention the carbon-containing layer present on the surface of the substrate is chemical-physically modified so that the inventive molecules can be bound thereto. For example, the surface can be modified by chemical modification such that molecules can be bound thereto specifically or selectively. Binding of the molecules, in particular of the biomolecules, to the chemically and/or physically modified carbon-containing layer can occur covalently or by means of affinity and/or bioaffinity chromatography using, e.g., amino acid sequences. When brought in contact with biological systems (cell cultures, tissue cultures, animals, human beings, etc), the presence of biologically active molecules on an inventive base body allows influence of the same.

Functionalising of the carbon-containing layer, preferably of the diamond layer, can be effected directly to the dangling bonds of the carbon or via a linker (according to the invention "linker" means a chemical compound comprising a functional group which docks or binds either directly to the pure and/or chemical-physically modified diamond layer or to the pure and/or chemical-physically modified carbon-containing layer or to the functional group of a further "linker"; the "linker" itself may have binding functionality). Several substances can also be bound to the carbon-containing surface.

In the present invention "binding functionality" refers to a functional group capable of binding molecules, preferably covalently, (e.g. biomolecules, proteins, hormones, growth factors, antibiotics, antibodies, cytostatics). A non-covalent binding, however, shall be strong enough to prevent the molecules bound to the carbon-containing layer from diffusing away or to allow for it to a little extent only.

According to the present invention a "functional group" means that part of a molecule which is responsible for binding a further molecule. These functional groups (e.g. amino groups, hydroxyl groups, carboxyl groups, sulfhydryl groups) are selected in correspondence with the biomolecules to be bound specifically, such as, e.g. antibodies, proteins, DNA, receptors, antibiotics and the like.

"Biomolecules" in the sense of the present invention comprise preferably nucleic acids, in particular DNA, cDNA, mtDNA, RNA, nRNA, mRNA, siRNA, rRNA, tRNA and PRNA, carbohydrates, in particular glucose, fructose, maltose, isomaltose, cellobiose, cellulose, gentiobiose, trehalose, lactose, saccharose, amylose, amylopectin, glycogen, pectin and chitin, lipids, in particular fatty acids and their alcohols, such as, e.g. myristic acid, palmitic acid, stearic acid, arachidic acid, behenic acid, palmetoleic acid, oleic acid, linoleic acid, arachidonic acid and erucic acid, sphinganines, such as, e.g. sphingosine, glycerine derivatives, phospholipids, such as, e.g. glycerophospholipids, steroids, in particular androgens, oestrogens, bile acid, corticosteroides (e.g. cortisone), progesterone, estrone, estradiol, ecdysone, strophantidin, sapogenines (e.g. digitogenins, diosgenin), steroid alkaloids (e.g. solanidine, tomatidine) and testosterone, viruses, in particular RNA viruses and DNA viruses, vectors, plasmides, lipoproteins, in particular LDL, HDL and VLDL, liposomes, amino acids, in particular L-alanine, L-arginine, L-asparagine, L-asparaginic acid, L-cysteine, L-glutamine, L-glutamic acid, glycine, L-histidine, L-isoleucine, L-leucine, L-lysine, L-methionine, L-phenylalanine, L-proline, pyrrolysine, L-selenocysteine, L-serine, L-threonine, L-tryptophan, L-tyrosine and L-valine, peptides and proteins, in particular enzymes, such as oxidoreductases, transferases, hydrolases, lyases, isomerases and ligases, antibodies, glycoproteins, peptidoglycans, proteglycans and proteins comprising at least one RGD motif, hormones, in particular peptide hormones, such as corticoliberin, folliberin, gonadoliberin, luliberin, melanoliberin, melanostatin, prolactoliberin, prolactostatin, somatoliberin, somatostatin, thyroliberin, choriogonadotropin, choriomammatropin, corticotropin, follitropin, gonadotropin, glumitocin, isotocin, lipotropin, lutropin, melanotropin, mesotocin, ocytocin (oxytocin), prolactin, somatotropin, thyrotropin, urogonadotropin, vasopressin, vasotocin, angiotensin, bradykinin, calcitonin, erythropoietin, gastrin, gastrine sulphate, glucagon, insulin, kallidin, pancreozymin, parathyrin, proangiotensin, relaxin, secretin, somatomedin and thymopoietin, prenols, polyprenols, prenol and polyprenol ethers, chinones, in particular tocochinone, plastochinone, ubichinone, menachinone and phyllochinone.

According to a preferred embodiment of the present invention the carbon-containing layer comprises a material selected from the group consisting of polymers, diamond, amorphous carbon, DLC (diamond-like carbon), graphite, nanotubes, nanowires, nanoparticles, fullerenes, pyrocarbon, glassy carbon, and mixtures thereof.

According to the invention any kind of layer containing carbon may be used for producing the base body described. Layers which contain carbon in $sp^2$ and/or $sp^3$ hybridisation may also be used.

Furthermore, carbon-containing layers, in particular diamond layers, can be applied on a substrate by galvanisation.

Further production methods can be divided into three main categories: "hot-filament method", "plasma method" and "hybrid method". Further alternative technologies exist, the use of which being not very common yet. An overview on different technologies can be found, e.g., in "Diamonad Films Handbook (edited by Jes Asmussen and D. K. Reinhard, Marcel Dekker, 2002, ISBN 0-8247-9577-6) or in "Synthetic Diamond—Emerging CVD Science and Technology" (edited by K. E. Spear and J. P. Dismukes, The Electrochemical Society Series, John Wiley & Sons, ISBN 0-471-53589-3).

The hot-filament method is based on the thermic stimulation of carbon-containing gases in the low-pressure region. In this method, different forms of carbon-containing layers deposit on a substrate. Subsequently, by thermal stimulation of a second gas—mostly hydrogen which is cleaved in atomic hydrogen—that components are etched away, in which the carbon is present in $sp^1$ or $sp^2$ hybridisation. Thus, when the parameters have been suitably chosen, it is possible to apply carbon-containing layers having a very high crystalline $sp^3$-hybrid portion. An embodiment of this technology is described in "Diamond and Related Materials" (P. K. Bachmann et al., 1991) and in JP 2 092 895. In the plasma method the gases are stimulated by stimulating plasma in the most different embodiments. Again, this technology is based on the above-described principle of depositing different carbon modifications which, on their part, are etched by the stimulated atomic hydrogen or other auxiliary gases, e.g. argon, so that in the net balance a high portion of $sp^3$-hybridised crystalline diamonds is obtained. Examples of this technology can be found in JP 1 157 498 and EP 0 376 694.

The hybrid methods use a combination of the two technologies described, i.e. thermal stimulation by filaments is supported by different kinds of plasma stimulation. One embodiment is described in U.S. Pat. No. 4,504,519.

With respect to the alternative technologies the arc-jet method is to be mentioned, wherein, by ignition of an electric arc, diamond layers can be deposited in a spacially narrow range mostly at a high rate, yet with a high $sp^2$ portion. One example of this technology can be found in EP 607 987 B.

A further preferred production method is described in AT 399 726 B. This is a modified hot-filament method, wherein gas stimulation can be effected with very high efficiency. With this method not only DLC layers and microcrystalline diamond layers can be produced, but also very pure nanocrystalline diamond layers which have proven to be particularly advantageous for the base body coating described here.

Preferably, the carbon-containing layer consists of polycrystalline, microcrystalline, nanocrystalline, ultrananocrystalline (John A. Carlisle and Orlando Aucielle, Ultrananocrystalline Diamond Properties and Applications in Biomedical Devices, The Electrochemical Society Interface, 12 (1), 28-31 (2003)) or monocrystalline diamond crystals.

In contrast to the surfaces mentioned in the prior art, the advantage of the inventive base body lies in the high biocompatibility, the high chemical stability, the renewability and in the defined chemical and physical modification/functionalisation of the carbon-containing surface, in particular when said surface comprises diamonds.

According to the invention, the term "biocompatibility" relates to the base body and entails that the base body, in its pure or chemically and/or physically modified form, does neither affect nor destroy the surroundings.

It is known from the literature that a pure diamond has biocompatible properties (Wensha Yang et al., *DNA modified nanocrystalline diamond thin-films as stable, biologically active substrates*; Nature Materials, Nov. 24, 2002, 253-257). By an appropriate pre-treatment of the diamond layers properties can be obtained which drastically and, in particular, permanently increases biocompatibility with respect to individual substances.

Due to the plurality of possible chemical modifications, in particular concerning diamond layers having a very broad electrochemical window for bindings of biomolecules (Nature Materials 3, 736-742 (1 Oct. 2004)), it is possible, e.g., to not only influence the degree of differentiation of cells, the cell's own expression of proteins, the secretion of chemotactic substances, i.e. of attractants, in a controlled manner, but also cell-defence mechanisms. The further possibility of specifically functionalising localised regions (with different properties) of the carbon-containing surface (particularly of a nanocrystalline (also polycrystalline, monocrystalline or ultrananocrystalline) diamond layer) extends the range of application for the binding of different biomolecules and/or proteins to a base-body-surface.

A further property of a nanocrystalline diamond surface, namely resistance against bacteria (Jakubowski W. et al., *Nanocrystalline diamond surface is resistant to bacterial colonization*, Diamond and Related Materials, Volume 13, Issue 10, October 2004, 1761-1763) is advantageous for the use of such base bodies.

According to a preferred embodiment the carbon-containing layer has a diamond-crystal proportion of at least 10%, at least 20%, at least 30%, at least 40%, at least 50%, at least 60%, at least 70%, at least 80%, at least 90%, at least 95%, at least 99%, in particular at least 99.5%.

The inventive properties could be proven already at a crystallite proportion of 10%. Thus, diamond-like carbon layers (DLC diamond-loke carbon) or a-C—H layers can also be used for coating substrates.

According to a further preferred embodiment the carbon-containing layer comprises diamond crystals with a crystallite size of 0.1 to 500 nm, preferably of 5 to 100 nm, in particular of 8 to 30 nm.

According to the invention it is favourable when the diamond layer has a crystallite size of less than 500 nm, preferably less than 300 nm, in particular less than 100 nm. These crystallite sizes are particularly advantageous when producing special morphologies of the base body. Other crystallite sizes may also be used according to the invention.

Preferably, the carbon-containing layer has a layer thickness of 0.1 nm to 50 μm, preferably 100 nm to 40 μm, in particular of 1 to 20 μm.

According to the invention the carbon-containing layer can be of different thickness, designed to be closed or not closed, in order to definitely achieve optimum results when functionalising and/or influencing a certain cell behaviour. This is why also smaller layer thicknesses with a yet not closed layer are absolutely possible for reducing costs.

According to a preferred embodiment the carbon-containing layer is electrically isolating or electrically conductive, wherein the electrical conductivity is conductible thanks to doping.

In this context, the volume material or the surface of the diamond is doped with elements known from the prior art, such as, e.g. boron or bromine or phosphor or nitrogen. Examples of such doped diamond layers can be found in "Thin Film Diamond" (edited by A. Lettington and J. W. Steeds, III. Royal Society (GB), 1994, ISBN 0412496305). Electrical conductivity can be of importance, e.g. during operations when electric voltage is fed for obliteration or the like.

According to a further preferred embodiment the carbon-containing layer on the base body is conductible thanks to adsorbed substances. Adsorbing hydrogen makes, e.g. the surface of a diamond, conductible (O. A. Williams and R. B. Jackman, Surface conductivity on hydrogen terminated diamond, Semicond. Sci. Technol. 18, 34-40 (2003)). Surface conductivity can be reached by saturating so-called dangling bonds by hydrogen. Such a hydrogen-terminated diamond surface shows hydrophobic character, whereas a termination of the dangling bonds by hydrogen causes a hydrophilic surface. Such a hydrogen-terminated surface is, again, not electrically conductive.

Preferably, the substrate comprises a material selected from the group consisting of metal, in particular gold, steel, molybdenum and titan, metal alloys, in particular steel alloys, molybdenum alloys and titan alloys, hard metals, cermets, metal oxides, mineral oxides, carbon, in particular pyrocarbon and graphite, semiconductors, polymer, plastics, in particular carbon-fibre reinforced and/or glass-fibre reinforced plastics, ceramics (e.g $Si_2N_3$, $Al_2O_3$, zirconium oxide), porcelain, glass, silica glass, silica gel, composite materials, nantubes, nanowires, nanoparticles, fullerenes, silicon compounds, in particular silicone, metal silicides and silicon carbide, sapphire, multi-matrix compounds (MMC), glassy carbon, cellulose, and mixtures thereof.

According to a preferred embodiment of the present invention at least one intermediate layer is applied between the substrate and the carbon-containing layer.

The intermediate layer preferably comprises a material selected from the group consisting of metal, metal alloys, metal oxides, metal carbides, silicon compounds, in particular metal silicides, such as cobalt silicide, and silicon carbide, mineral oxides, graphite, semiconductors, polymer, plastics, ceramics, glass, silica glass, silica gel, steel, steel alloys, composite materials, nanotubes, nanowires, nanoparticles, fullerenes, pyrocarbon, glassy carbon, and mixtures thereof.

An intermediate layer is suitable for substrates which have a different thermal expansion coefficient to the carbon-containing layer, in particular the diamond layer. Such an intermediate layer allows for layer tensions to be relieved and, thus, for better layer adherence. Furthermore, thanks to intermediate layers, it is possible to coat substrates which would chemically bind to the carbon layer. One example therefor are hard metals, where, by an appropriate intermediate layer, the cobalt components of the hard metal are chemically deactivated and/or covered (passivated), thus either preventing formation of cobalt carbide or displacing said components to regions not active for the carbon layer. According to the invention several intermediate layers may be provided so that a multilayer system is formed on the substrate. The multilayer may comprise, e.g. a diamond, DLC and a polymer layer.

According to a further preferred embodiment the carbon-containing layer comprises hydrophilic and/or hydrophobic regions.

Regions may be provided on the surface of the carbon-containing layer which may have different chemical and/or physical properties, such as, e.g. hydrophilic, hydrophobic or differently functionalised regions. These regions can be structured by means of certain technologies (masks, lithography, electron beam lithography) and can be produced in a controlled manner by subsequent termination, e.g. in oxygen or hydrogen plasma, wet chemically, in an ozone atmosphere or in an atomic hydrogen atmosphere. Due to an appropriate surface termination, e.g. with respect to diamond layers on the so-called dangling bonds, a hydrophobic surface property may be provided by hydrogen and a hydrophilic one by oxygen. In this context, the surface may be designed in a manner that the hydrophilic regions, onto which the biomolecules are applied, are bordered by hydrophobic regions. Thus, it is possible to provide special—different—biomolecules and/or proteins in a localised way what had been not possible so far. Hydrophilic and/or hydrophobic regions on the diamond surface are produced according to the methods disclosed in the prior art (US 2002/045270 A1). According to the invention said structuring is not restricted to the properties of hydrophoby and hydrophily and may also comprise any other physical and/or chemical properties. In particular, the functionalisation can, of course, also be structured directly.

Preferably, in this case, the hydrophilic and hydrophobic regions of the carbon-containing layer are structured.

According to a preferred embodiment the chemically and/or physically modified carbon-containing layer has at least one binding functionality selected from the group consisting of polar, apolar, hydrophobic, hydrophilic, ionic, affine, specific, meta-complexing groups, or mixtures thereof.

According to the invention "affine" groups include all those functional groups and/or molecules which have an affinity to other chemical compounds and groups.

"Specific" functional groups comprise all chemical compounds capable of specifically binding other chemical compounds and groups. Examples therefor in this context are antibody-antigen, enzyme-substrate, enzyme-inhibitor and protein-ligand compounds.

Preferably, the carbon-containing layer comprises hydrogen atoms, halogens, hydroxyl groups, carbonyl groups, aromatic ring systems, sulphur, sulphur derivatives, grignard compounds, amino groups, epoxides, metals or carbon chains, on the surface due to chemical modification.

According to a further embodiment the carbon-containing layer has at least one binding functionality selected from the group consisting of carbon double bonds, epoxides, halogens, amino groups, hydroxy group, acid groups, acid chlorides, cyanide groups, aldehyde groups, sulphate groups, sulphonate groups, phosphate groups metal-complexing groups, thiethers, biotin, thiols, and mixtures thereof, on the surface.

Preferably, the carbon-containing layer is covalently modified with hydrogen (—H) (Toshiki Tsubota et al., *Reactivity of the hydrogen atoms on diamond surface with various radical initiators in mild condition*, Diamond and Related Materials, 11 (7) 1360-1365 (2002)), halogens (—Cl, —Br, —I, —F), hydroxyl function (—OH), carbonyl function (=O), aromatic ring systems, sulphur and sulphur derivatives, grignard compounds (—MgBr), amines (—NH$_2$), epoxides, metals (—Li) or carbon chains. The chemical-physically modified carbon-containing layer optionally has binding functionalities, thus rendering possible direct covalent binding of biomolecules or creating the prerequisite for a further functionalising via a linker.

Preferably, the carbon-containing layer is chemically modified with at least one linker, wherein the linker has at least one binding functionality preferably selected from the group consisting of carbon double bonds, epoxides, halogens, amino groups, hydroxy group, acid groups, acid chlorides, cyanide groups, aldehyde groups, sulphate groups, sulphonate groups, phosphate groups, metal-complexing groups, thiethers, biotin, thiols, and mixtures thereof.

Thanks to directly applying functional groups on the carbon-containing surface, it is possible to covalently or non-covalently bind the desired biomolecules, such as, e.g. peptides, proteins, nucleic acids, antibiotics and other chemical substances, to the base body.

In this context, the linker(s) is/are bound to the chemical-physically modified carbon-containing layer, e.g. a diamond layer, using methods known per se from the prior art (M. A. Fox and J. K. Whitesell, Organische Chemie, 1995, pp. 255, 297-298, 335-338, 367-368, 406-408, 444-446, 493-496, 525-526, 550-551, 586-587, 879-884) (for example, a compound containing a carbon double bond is bound to the diamond layer by photochemical reactions (Todd Strother et al., *Photochemical Functionalisation of Diamond Films*, Langmuir 18 (4): 968-971 (2002)).

According to a preferred embodiment the molecule is selected from the group consisting of proteins and fragments thereof, in particular antibodies, growth factors and differentiation factors, carbohydrates, hormons, antibiotics, cytostatics, and combinations thereof.

The proteins and/or biomolecules which are applied on the surface of a base body according to the invention can be of any nature, such as, e.g. antibiotics, growth factors, signal molecules and antibodies. Introducing such proteins and/or biomolecules bound to the carbon-containing surface of an inventive base body, preferably of a substrate coated with a monocrystalline, microcrystalline or nanocrystalline diamond layer, allows by definition for a local effect without diffusion away, whereby a systemic effect can be prevented.

For example, a number of immunosuppressives can be bound to the inventive base body, e.g. glucocorticoids, ciclosporines/tacrolimus, rapamycin, methotrexate, azathioprine, mizoribine, mycophenolate mofetil, brequinar, leflunomide, deoxyspergualine, polyclonal and/or monoclonal antilymphocytes antibodies: ALS, ALG, ATG, 1-Anti-CD3 (OTK3), Anti-TCR, Anti-CD4, Anti-CD25, Anti-LFA-1, Anti-ICAM-1, Anti-IgE.

Preferably, on the base body, proteins, in particular from the TGF-β superfamily, are bound to the chemically and/or physically modified carbon-containing layer.

Growth factors are well suited for binding to an inventive base body, as it thus is rendered possible to, e.g. influence growth of the tissue surrounding the base body in a biological system.

According to a further preferred embodiment bone morphogenetic proteins (e.g. BMP-2) are bound to the chemically and/or physically modified carbon-containing layer on the base body.

Preferably, the base body is designed as implant, cell-growth vessel or surgical/endosurgical instrument.

A further object of this invention is to accellerate the time it takes for implants to settle. One possibility for shortening the time of settling is to use growth factors in implantology. The most important osteogenous growth and differentiation factors include bone morphogenetic proteins (BMP), which belong the TGF-gamma superfamily and of which at least 18 different ones exist (BMP-2 to 18). At present, BMP-2 and -7 are the most important of this group, which lead to induction and differentiation of human osteoblasts from bone marrow stromal cells. Numerous animal experiments could prove this effect. Clinical research concentrates on the use of cytokine for regeneration of bone defects. One approach is the direct application of BMPs—in combination with different carrier materials—on a bone defect. In this context a significantly improved bone regeneration could be achieved in experimental works on animals. In implantology cytokines are primarily used in experiments, as a systemic effect could have not been prevented so far by the methods used. Introducing proteins into the shaft of the implant, drying proteins onto the implant (AU 688406; WO 2004/024199) or using biomimetic coatings (WO 2004/024201; U.S. Pat. No. 6,129,928; CN 139318) is primarily used.

Therefore, a further aspect of the invention relates to the use of the inventive base body as implant. The uses illustrated apply to implants as well as to prothesis and artificial joints anchored in the bone, as here similar requirements can be set out. Also here the settling behaviour can be influenced.

Implant surfaces, e.g. of parts in traumatology, which shall not knit with the bone, do not have a structured and/or porous surface but are smooth. A carbon layer, in particular a nanocrystalline diamond layer, is suitable for obtaining such a topography which can be selectively structured and/or functionalised in order to ensure the desired local influence. All foreign elements introduced into the inner of the body from outside are referred to as implant and/or surgical/endosurgical instrument, wherein the implant may be in the body for a few minutes or hours during a surgical intervention or up to years. Moreover, auxiliary means, such as e.g. screws, bolts, are referred to as "implants".

According to the invention an "implant" consists of a substrate and a carbon-containing layer. The desired molecules, preferably biomolecules, are applied onto said implant. Said implants can be used in both human beings and animals.

According to the invention growth factors can also be bound covalently to an implant coated with carbon layers, in particular with nanocrystalline diamond layers and, thus, a local effect, i.e. a better and accellerated osseointegration, especially in the weak bone stock, can be achieved. A systemic effect can therewith be avoided, whereby a routine clinical use thereof could be possible. In addition to growth factors, antibiotics, e.g., could be bound onto the implant by means of carbon-containing layers, thus reducing the risk of a post-surgical infection.

According to a further preferred embodiment the implant is selected from the group consisting of dental implant, knee implant, hip implant, bolts, screws, nails, cardiac valves, cathoders, stent, plates, cranial plates, splints and prostheses.

A further aspect of the present invention relates to the use of the inventive base body as surgical/endosurgical instrument.

Usually, when being used, surgical and endosurgical instruments come in direct contact with human and/or animal tissue. In order to avoid or reduce undesired side effects (e.g. rejection effects) and to provoke desired effects (e.g. active-substance transport to the site of intervention), such instruments can be coated with an inventive modified carbon-containing layer. A further advantage is the longer durability of these instruments, since the carbon layers, in particular diamond layers, have a particularly high degree of hardness and a higher physical and chemical resistance. Special biomolecules may also be bound to, in order to ensure sterility of the instruments (e.g. by binding molecules capable of rejecting bacteria).

Preferably, the surgical/endosurgical instrument is designed as endoscope.

A further aspect of the present invention relates to the use of the inventive base body as cell-growth vessel.

The inventive base body may also be designed as cell-growth vessel for culturing cells in vitro, wherein the definition "cell-growth vessel" includes containers which may be locked up as well as cell-growth dishes and cell-growth substrates. Substances capable of influencing growth of the cells cultured, can be introduced into the cell-culture vessels by means of appropriately functionalised carbon layers, preferably microcrystalline or nanocrystalline diamond layers. Thus, cell-growth studies can be conducted or growth rates can also be increased. According to the invention containers, such as fermenters, cell-culture plates, cell-culture dishes, cell-culture bottles, cell-culture tubes and the like, known from the prior art and routinely used in laboratories and in production, are suitable.

The inventive cell-growth vessels and implants are especially well-suited for tissue engineering, wherein cells can be prompted to grow and differentiate on the functionalised carbon-containing layer, whereby tissue, e.g. muscle tissue, skin and other organs, can be produced both in vitro (cf., e.g., Oberpenning F. et al., Nature Biotechnology (1999), 17:149-155) and in vivo (cf., e.g., U.S. Pat. No. 5,716,404), wherein an inventive implant is used in vivo. Thus, the inventive base body serves as substrate and/or matrix for cell growth (Godbey W T. et al., Ann NY Acad. Sci. (2002), 961:10-26; Atala A. Rejuvenation Res. (2004), 7:15-31).

According to the invention cell-growth vessels, in particular when used for tissue engineering, could also have a structuring to allow for forming of special forms. In this context, regions can be defined, in which certain growth conditions prevail, whereby many different growth forms can be realised in one dish (this, e.g., facilitates comparisons). The biomolecules used can be adapted on the surface to the stage of differentiation such that propagation etc. can be influenced. Due to the functionalised carbon surface, cells can faster pass to three-dimensional growth, as the surface is no "barrier" but—as in the surrounding culture medium—offers an appropriately functionalised surface.

The invention will be described in more detail by way of the following figures and examples, yet without being restricted thereto.

DESCRIPTION OF THE INVENTION

Example 1

Dental Implant

Figure 1:
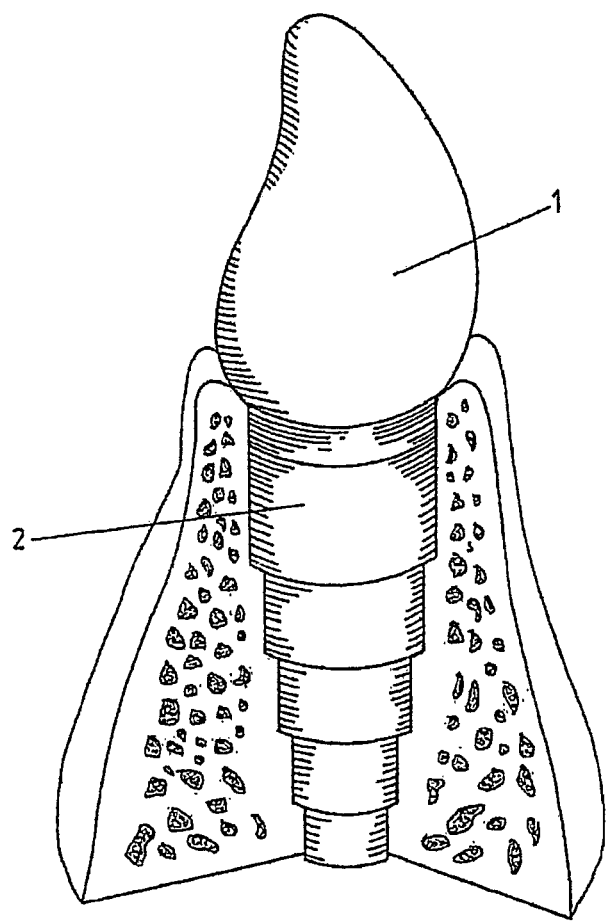
FIG. 1 shows an artificial tooth made of ceramics 1, which is screwed into the jaw by means of a dental implant made of a titan alloy 2.
Figure 2:
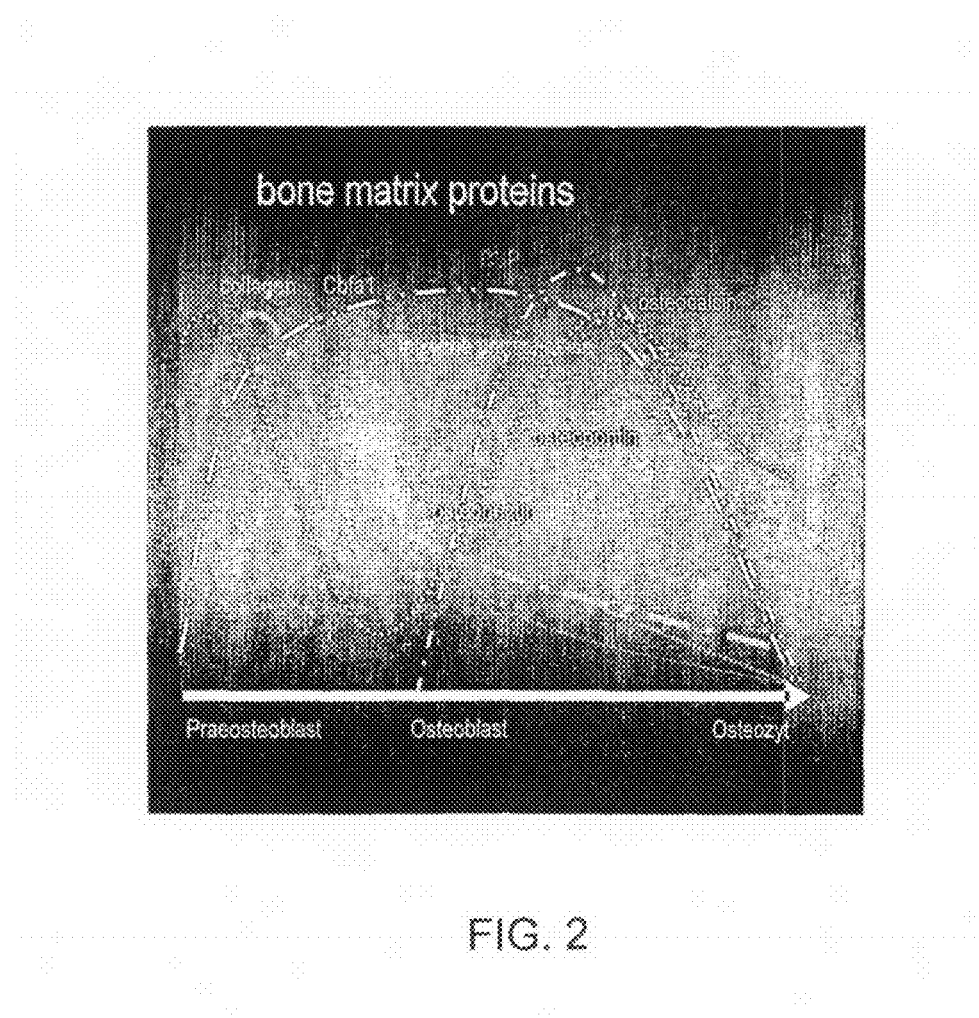
FIG. 2 is a schematical illustration of the most important bone matrix proteins in their timely occurence during differentiation from preosteoblasts to the mature bone cell. Due to the different occurence in terms of time and the thus possible addiation, differentiation to the bone-forming cell can be influenced in every stage of maturing.
Figure 3:
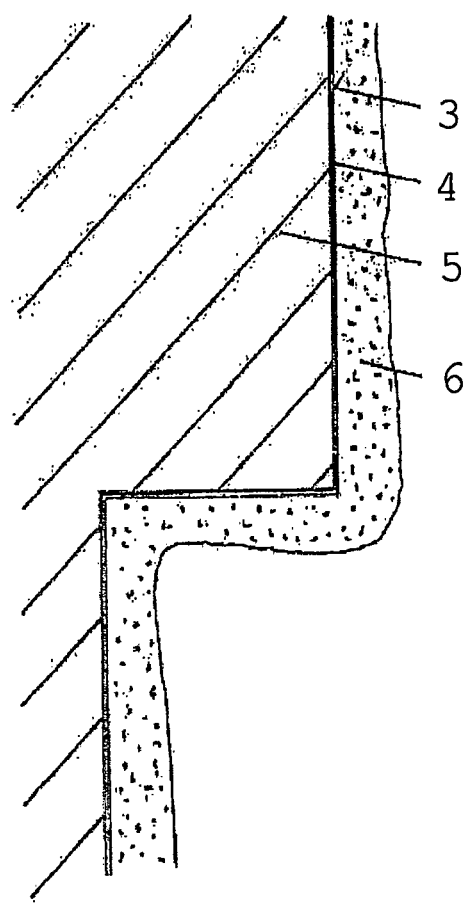
FIG. 3 shows a nanocrystalline, diamond-coated 3 base body surface 4 which has been chemically modified 5 by a protein (BMP2), and, thus accellerate 6 local bone formation in the jaw.
Figure 4:
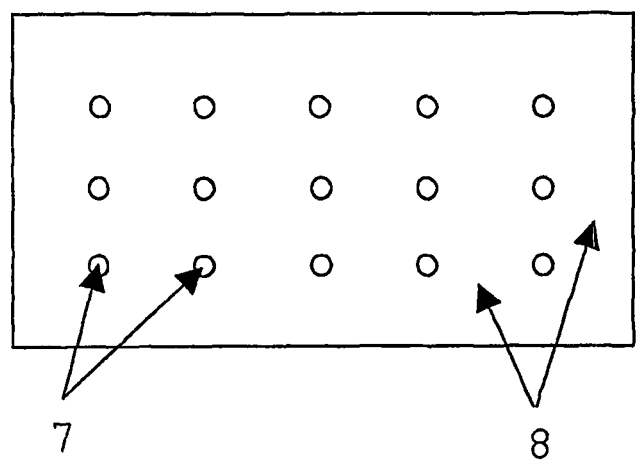
FIG. 4 shows a structured nanocrystalline diamond layer on a substrate (hydrophilic regions—localised in circle 7 and hydrophobic regions in the surroundings of circular regions 8) as basis for binding of different proteins, and, thus, local concentration variations are possible.
Figure 5:
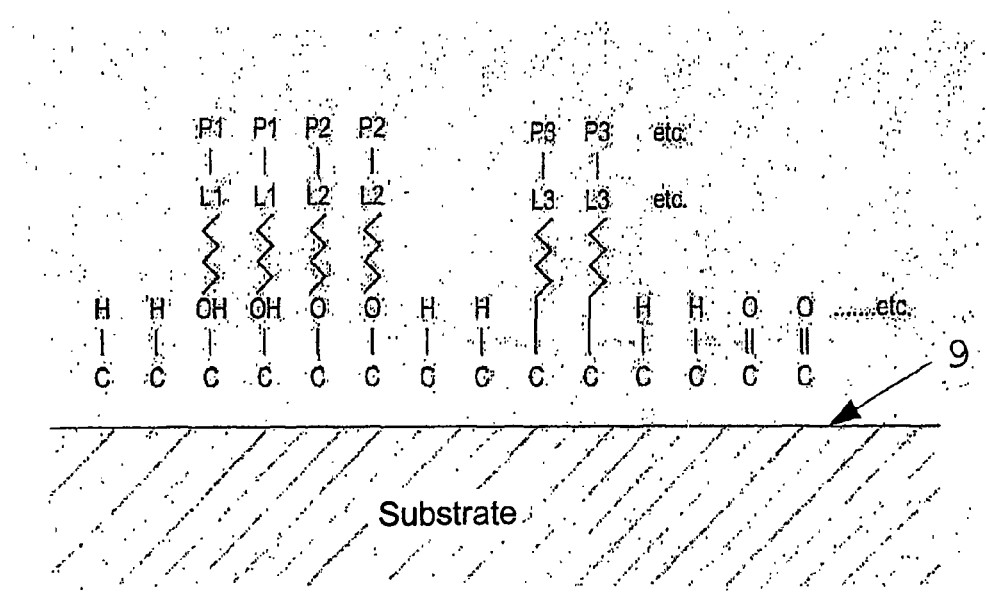
FIG. 5 shows a substrate having a diamond layer 9 with a structured surface which, when localised, has an oxygen or hydrogen termination. The corresponding linker/functional group (L1, L2) is the binding member for binding of the protein desired (P1 or P2).

Enoral implants, i.e. mounted in the jaw (FIG. 1), and extraoral implants, i.e. mounted on the facial part of the scull, have proven to be good achoring elements with respect to rehabilitation of the chewing apparatus after tooth loss, traumatic or tumor-related defects, and to treatment of face defects after tumour surgeries or inherited anomalia by face protheses. A crucial factor for the success of endosseous implants, i.e. implants anchored in the bone, is the degree of bone settling, the so-called osseointegration. In this case, osseointegration decisively depends on the local bone condition. Consequently, the success of implants is reduced in the pre-radiated receiving bed. The reduced blood circulation in this regions leads to a reduced regeneration potential of the bone after surgical manipulation so that osseointegration of implants may also be threatened. Different surface coatings have therefore been designed to enhance osseointegration (Buser D. et al., J Dent Res (2004) 83:529-533; Thorwarth M et al., Mund Kiefer Gesichtschir (2004) 8:250-255; Cochran D L et al., J Periodontol (1999) 70: 139-150).

Example 2

Modification of a Base Body

The base body is given into an illumination chamber, nitrogen being run theretrough. The cover (lid) of the illumination chamber constsits of silica glass. The linker substance, preferably protected trifluoroacetamide with long-chained, unsaturated amine, in particular 3-aminopropene, is applied on the H-terminated carbon-containing layer of the base body and is illuminated with UV light for 8 to 12 hours. The protective group of the trifluoroacetamide is removed by a methanolic HCl solution at 65° C. Then, the protein, preferably from the TGF-β superfamily, in particular bone morphogenetic protein (e.g. BMP-2) is covalently bound on the amine of the linker.

The invention claimed is:
1. An implant, comprising:
   a substrate; and
   a carbon-containing layer at least partially coating said substrate, said carbon-containing layer formed of at least 80% diamond crystals and said carbon-containing layers being at least partially functionalized with a growth factor, protein, or peptide bound to said carbon-containing layer either directly or via at least one linker or functional group.
2. The implant according to claim 1, wherein said carbon-containing layer includes a material selected from the group consisting of polymers, diamond, amorphous carbon, diamond-like carbon, graphite, nanotubes, nanowires, nanoparticles, fullerenes, pyrocarbon, glassy carbon, and mixtures thereof.
3. The implant according to claim 1, wherein said carbon-containing layer includes diamond crystals selected from the group consisting of polycrystalline, microcrystalline, nanocrystalline, ultrananocrystalline and monocrystalline diamond crystals.
4. The implant according to claim 1, wherein said carbon-containing layer has a diamond-crystal proportion selected from the group consisting of at least 90%, at least 95%, at least 99%, and at least 99.5%.
5. The implant according to claim 1, wherein said carbon-containing layer has diamond crystals with a crystallite size of 5 to 100 nm.
6. The implant according to claim 1, wherein said carbon-containing layer has diamond crystals with a crystallite size of 8 to 30 nm.
7. The implant according to claim 1, wherein said carbon-containing layer has a layer thickness of 0.1 nm to 50 μm.
8. The implant according to claim 1, wherein said carbon-containing layer has a layer thickness of 100 nm to 40 μm.
9. The implant according to claim 1, wherein said carbon-containing layer has a layer thickness of 1 to 20 μm.
10. The implant according to claim 1, wherein said carbon-containing layer is one of electrically isolating and electrically conductive.
11. The implant according to claims 1, wherein said substrate contains a material selected from the group consisting of metal, gold, steel, molybdenum, titan, metal alloys, steel alloys, molybdenum alloys, titan alloys, hard metals, cermets, metal oxides, mineral oxides, carbon, pyrocarbon, graphite, semiconductors, polymer, plastics, ceramics, porcelain, glass, silica glass, silica gel, composite materials, nanotubes, nanowires, nanoparticles, fullerenes, silicon compounds, silicone, metal silicides, silicon carbide, sapphire, multi-matrix compounds, glassy carbon, and mixtures thereof.
12. The implant according to claim 1, further comprising at least one intermediate layer applied between said substrate and said carbon-containing layer.
13. The implant vessel according to claim 12, wherein said intermediate layer contains a material selected from the group consisting of metal, metal alloys, metal oxides, metal carbides, silicon compounds, metal silicides, cobalt silicide, silicon carbide, mineral oxides, graphite, semiconductors, polymer, plastics, ceramics, glass, silica glass, silica gel, steel, steel alloys, composite materials, nanotubes, nanowires, nanoparticles, fullerenes, pyrocarbon, glassy carbon, and mixtures thereof.
14. The implant according to claim 1, wherein said carbon-containing layer includes at least one of hydrophilic regions and hydrophobic regions.
15. The implant according to claim 14, wherein said hydrophilic regions and said hydrophobic regions of the carbon-containing layer are structured.
16. The implant according to claim 1, wherein said carbon-containing layer is at least one of a chemically and a physically modified carbon-containing layer having at least one binding functionality selected from the group consisting of polar, apolar, hydrophobic, hydrophilic, ionic, affine, specific, meta-complexing groups, and mixtures thereof.
17. The implant according to claim 1, wherein said carbon-containing layer includes one of hydrogen atoms, halogens, hydroxyl groups, carbonyl groups, aromatic ring systems, sulphur, sulphur derivatives, grignard compounds, amino groups, epoxides, metals and carbon chains, by chemical modification.
18. The implant according to claim 1, wherein said carbon-containing layer has at least one binding functionality selected from the group consisting of carbon double bonds, epoxides, halogens, amino groups, hydroxy group, acid groups, acid chlorides, cyanide groups, aldehyde groups, sulphate groups, sulphonate groups, phosphate groups metal-complexing groups, thiethers, biotin, thiols, and mixtures thereof.
19. The implant according to claim 1, wherein said carbon-containing layer is chemically modified with at least one linker.
20. The implant according to claim 19, wherein said at least one linker has at least one binding functionality.
21. The implant according to claim 20, wherein said binding functionality is selected from the group consisting of carbon double bonds, epoxides, halogens, amino groups, hydroxy group, acid groups, acid chlorides, cyanide groups, aldehyde groups, sulphate groups, sulphonate groups, phosphate groups, metal-complexing groups, thiethers, biotin, thiols, and mixtures thereof.
22. The implant according to claim 1, wherein said carbon containing layer growth factor, protein, or peptide is a biomolecule bound to said carbon-containing layer one of directly or via at least one linker or functional group, said biomolecule is selected from the group consisting of nucleic acids, DNA, cDNA, mtDNA, RNA, nRNA, mRNA, siRNA, rRNA, tRNA, pRNA, carbohydrates, glucose, fructose, maltose, isomaltose, cellobiose, cellulose, gentiobiose, trehalose, lactose, saccharose, amylose, amylopectin, glycogen, pectin, chitin, lipids, fatty acids, fatty acid alcohols, myristic acid, palmitic acid, stearic acid, arachidic acid, behenic acid, palmetoleic acid, oleic acid, linoleic acid, arachidonic acid, erucic acid, sphinganines, sphingosine, glycerine derivatives, phospholipids, glycerophospholipids, steroids, androgens, oestrogens, bile acid, corticosteroides, cortisone, progesterone, estrone, estradiol, ecdysone, strophantidin, sapogenines, digitogenins, diosgenin, steroid alkaloids, solanidine, tomatidine, testosterone, viruses, RNA viruses, DNA viruses, vectors, plasmides, lipoproteins, LDL, HDL, VLDL, liposomes, amino acids, L-alanine, L-arginine, L-asparagine, L-asparaginic acid, L-cysteine, L-glutamine, L-glutamic acid, glycine, L-histidine, L-isoleucine, L-leucine, L-lysine, L-methionine, L-phenylalanine, L-proline, pyrrolysine, L-selenocysteine, L-serine, L-threonine, L-tryptophan, L-tyrosine, L-valine, peptides, proteins, enzymes, oxidoreductases, transferases, hydrolases, lyases, isomerases, ligases, antibodies, glycoproteins, peptidoglycans, proteoglycans, proteins containing at least one RGD motif, hormones, peptide hormones, corticoliberin, folliberin, gonadoliberin, luliberin, melanoliberin, melanostatin, prolactoliberin, prolactostatin, somatoliberin, somatostatin, thyroliberin, choriogonadotropin, choriomammatropin, corticotropin, follitropin, gonadotropin, glumitocin, isotocin, lipotropin, lutropin, melanotropin, mesotocin, ocytocin (oxytocin), prolactin, somatotropin, thyrotropin, urogonadotropin, vasopressin, vasotocin, angiotensin, bradykinin, calcitonin, erythropoietin, gastrin, gastrin sulphate, glucagon, insulin, kallidin, pancreozymin, parathyrin, proangiotensin, relaxin, secretin, somatomedin and thymopoietin, prenols, polyprenols, prenol ethers, polyprenol ethers, chinones, tocochinone, plastochinone, ubichinone, menachinone, phyllochinone, growth factors, differentiation factors, antibiotics, cytostatics, and combinations thereof.

23. The implant according to claim 1,
wherein said carbon-containing layer is at least one of a chemically and physically modified carbon-containing layer; and
further comprising proteins bound to said chemically and/or physically modified carbon-containing layer.

24. The implant according to claim 23, wherein said proteins are selected from the TGF-β superfamily.

25. The implant according to claim 1,
wherein said carbon-containing layer is at least one of a chemically and physically modified carbon-containing layer; and
further comprising bone morphogenetic proteins bound to said chemically and/or physically modified carbon-containing layer.

26. The implant according to claim 25, wherein said bone morphogenetic proteins are BMP-2.

27. The implant according to claim 1, wherein the implant is selected from the group consisting of dental implants, knee implants, hip implants, bolts, screws, nails, cardiac valves, catheders, stents, plates, cranial plates, splints and prostheses.

* * * * *